United States Patent [19]

Caratan

[11] Patent Number: Plant 6,421

[45] Date of Patent: Nov. 29, 1988

[54] GRAPEVINE, ROUGE

[75] Inventor: George L. Caratan, Delano, Calif.

[73] Assignee: Anton George Caratan, Delano, Calif.

[21] Appl. No.: 8,643

[22] Filed: Jan. 29, 1987

[51] Int. Cl.[4] ..... A01H 5/03

[52] U.S. Cl. ..... Plt./47

[58] Field of Search ..... Plt. 47

*Primary Examiner*—Robert E. Bagwill

*Attorney, Agent, or Firm*—Worrel & Worrel

[57] ABSTRACT

A new and distinct variety of grapevine denominated varietally as "Rouge" generally resembling the Emperor grapevine (unpatented) but characterized as to novelty by producing grapes which are ready for commercial harvesting approximately September 10 to October 15 at Delano, Calif. and which furthermore produce berries which are substantially greater in size and which have a different color than that of the Emperor variety of grapevine.

1 Drawing Sheet

BACKGROUND OF THE NEW VARIETY

The present invention relates to a new and distinct variety of grapevine denominated varietally as "Rouge", and more particularly to a grapevine which is somewhat similar in physical characteristics to the Emperor Grapevine (unpatented), from which it was derived as a sport, and the Christmas Rose Grapevine (unpatented) with which it matures in approximately the same season; but from which it is distinguished therefrom as to novelty by producing berries which ripen for commercial harvesting approximately two to three weeks earlier than the Emperor Grapevine, and which differs from the Christmas Rose Grapevine (unpatented), in color, leaf shape, fruit texture and flavor.

The Emperor Grapevine (unpatented) is well known as a vigorous producer of red seeded table grapes. Furthermore, the berries of the Emperor Grapevine (unpatented) have long been known for their excellent eating quality, delicious flavor, and shelf life under refrigeration.

It has long been recognized that it would be desirable to have a grapevine that somewhat resembles the Emperor Grapevine but which bears fruit which ripens for commercial harvesting earlier in the season, whereby the commercial demand for such a red seeded table grape can be effectively satisfied over a greater period of time.

The grapevine of the present invention is noteworthy in ripening extremely late in the season, approximately September 15 through October 15 at Delano, Calif., with most of the crop being ready for commercial harvest approximately September 21 through September 27.

ORIGIN AND ASEXUAL REPRODUCTION OF THE NEW VARIETY

The present variety of grapevine was discovered in 1971 as a sport of an Emperor Grapevine (unpatented) which was growing within the cultivated area of a commercial vineyard of Emperor Grapevines owned by the inventor and located near Road 160 and Avenue 8 in Delano, Calif. The subject variety was observed at that time to have desirable characteristics and it was thereafter asexually reproduced by the inventor, at the same vineyard, by taking cuttings of the instant variety and thereafter planting them, on their own roots, and growing them to maturity. This first asexual reproduction occurred during the 1972 growing season. This first asexual propagation has been continuously observed by the inventor and it has been subsequently determined that the progeny produced possess the same distinctive characteristics as the original sport.

BRIEF DESCRIPTION OF THE DRAWINGS

The drawing is a color photograph of a characteristic twig bearing typical leaves, two bunches of grapes showing their external coloration sufficiently mature for harvesting and shipment, several immature leaves of the subject variety and several berries halved in the axial plane, and transverse to the axial plane, to illustrate the flesh coloration and seed coloration, all of the subject variety.

DETAILED DESCRIPTION

Referring more specifically to the pomological details of this new and distinct variety of grapevine, the following has been observed under the ecological conditions prevailing in the vineyard of the inventor located in Delano, Calif. All major color code designations are by reference to the Maerz and Paul Dictionary of Color, Second Edition, 1950. Common color names are also used occasionally.

VINE

Size:

*Generally.*—Large.

Form: Upright growth; open to mediumly dense; tender; the subject variety was described as it was growing in the cultivated area of the commercial orchard of the inventor. The variety was bilateral cordon-trained and spur pruned. The instant variety also received standard cultural practices, including cluster thinning by tipping.

Vigor: Average to vigorous; the variety displays growth characteristics similar to the Emperor variety of grapevine (unpatented).

Productivity: Productive. The average shoot commonly produces one cluster of grapes per shoot. An average vine typically produces 30 to 35 shoots.

Trunk:

*Size.*—Generally — large, the vines of the subject variety were trained to a trunk height of approximately 31 inches (79 cm.) above the vineyard floor.

*Trunk diameter.*—Generally — average, approximately 2.4 inches (57.15 mm.) as measured at just below the cordon point, approximately (60.555 cm.) above the vineyard floor.

*Bark — texture.*—Loose and shreddy.

*Bark — color.*—Wild honey (Plate 13, C-9).

Canes:

*Length.*—Long; approximately 284.2 cm.

*Numbers.*—Average.

*Thickness.*—Medium, the average diameter is approximately 11.6 mm.

*Color.*—Cafe cream (Plate 14, D-8 to Plate 14, G-9, page 51.).

*Form.*—Straight.

Nodes:

*Numbers.*—An average shoot has approximately 28.

*Form.*—Enlarged.

Internodes:

*Length.*—Medium; the average internode length is variable; the average length is approximately 11.64 cm.

Tendrils:

*Generally.*—Intermittent or discontinuous.

*Thickness.*—Medium.

*Length.*—Long, approximately 4.6 inches, (116 mm.).

*Diameter.*—Approximately 0.1 inches (2.3 mm.).

*Form.*—Trifurcated with a few bifurcated tendrils.

*Texture.*—Smooth.

*Numbers.*—Abundant.

*Numbers of branches.*—Variable; two to three branches were found, the majority of grapevines however, have three branches.

Flowers:

*Generally.*—Fertile.

*Form.*—Open, with well developed erect stamens which produce abundant pollen. The flowers of the subject variety have a well-developed pistil and a creme colored stigma.

*Date of bloom.*—Generally — average as compared with other varieties. In 1986 full bloom was achieved on May 10 through 11, 1986. It should be understood that the date of bloom is approximately 10 to 14 days earlier than the normal date of bloom inasmuch as 1986 was considered to be an early year in Delano, Calif.

LEAVES

Size:

*Generally.*—Average as compared with other varieties.

*Average length.*—Approximately 5.6 inches, (14.34 cm.).

*Average width.*—Approximately 6.9 inches, (17.51 cm.).

*Average thickness.*—Medium, approximately 0.15 inches, (3.79 mm.).

*Form.*—Generally — round.

Color:

*Dorsal surface.*—Mature growth — dark green, (Plate 22, K-7, page 67).

*Ventral surface.*—Mature growth — pale green, (Plate 21, J-6, page 65).

*Dorsal surface.*—Immature growth — Hyacinth red, (Plate 4, F-11).

*Ventral surface.*—Immature growth — Nasturiam, (Plate 4, I-12).

Texture:

*Dorsal surface.*—Mature growth — average.

*Ventral surface.*—Mature growth — downy.

*Immature growth.*—New shoot tips — glabrous.

Color:

*New shoot tips.*—Reddish purple.

Petioles:

*Mature and immature leaves.*—Color — green with light purple coloration, (Plate 4, J-4). The petioles of the mature and immature leaves display the light purple coloration.

*Length.*—Generally — relatively long, approximately 6.3 inches (15.96 cm.).

Lobes:

*Numbers.*—Variable, three to five lobes may be present, usually three distinct lobes are evident, however, in some leaves five well defined lobes may be found.

*Terminal lobe.*—Form — variable, acute and occasionally acuminate.

Petiolar sinus:

*Depth.*—Deep.

*Width.*—Wide.

*Form.*—Open and substantially U-shaped.

Basal sinus:

*Depth.*—Very shallow, occasionally absent.

*Width.*—Narrow.

Lateral sinus:

*Depth.*—Average, occasionally shallow.

*Width.*—Narrow, occasionally overlapping.

Margin:

*Generally.*—Form — dentate.

Teeth:

*Size.*—Variable, shallow and occasionally deep.

*Width.*—Narrow.

*Form.*—Variable; narrow; mostly convex; occasionally pointed teeth may be found.

FRUIT

Maturity when described: Ripe for harvesting; in 1985 the harvesting date for the majority of the crop was September 21. In 1986, the harvesting date for the majority of the crop was September 27. The instant variety can be harvested from a date as early as September 10 through as late as October 15. The date of ripening is somewhat late as compared with other varieties.

Keeping quality: Not tested, however all the evidence appears to indicate that the variety has a shipping quality comparable to the Emperor Grapevine (unpatented).

Cluster:

*Size.*—Very large; the average weight is approximately 3.6 lbs. (1645.3 grams).

*Length.*—Generally — long, approximately 8–14 inches, (23–36 cm.) at bloom time.

*Shape.*—Conical; occasionally round or tapering; regular, and double shouldered.

*Density.*—Generally — medium, the clusters are well filled but not compact. On average, six to eight main laterals make up a cluster.

Peduncle:

*Length.*—Long; the average length is approximately 1.6 inches (40.78 mm.).

*Thickness.*—Generally — average, approximately 0.24 inches (6.1 mm.).

Pedicel:

*Generally.*—There is a strong attachment between the berry and the pedicel.

*Length.*—Average; the average length is approximately 0.36 inches, (9.13 mm.).

*Thickness.*—Generally — average; occasionally slender; approximately 0.055 inches, (1.42 mm.).

*Warts.*—Present; numbers — few.

*Rachis.*—Color — green, (Plate 14, K-1).

*Brush.*—Length — average; the average length is approximately 0.14 inches, (3.56 mm.).

*Color.*—Yellow.

Berry:

*Generally.*—The shells are strongly to mediumly adherent. No shattering problem is evident.

*Size.*—Generally — large; average weight per berry is approximately 9.85 grams.

*Uniformity.*—Variable; the berry of the subject variety is uniform in size but shows some variability with respect to the shape of the berry, from oval, which most of the berries assume, to some occasionally appearing roundish.

*Color.*—Red, (Plate 7, L-6, page 37).

*Bloom.*—Generally — average.

Skin:

*Generally.*—The skin of the instant variety adheres to the pulp.

*Thickness.*—Average.

*Texture.*—Medium.

Flesh:

*Color.*—White and translucent.

*Texture.*—Average; tender, meaty and crisp.

*Juice production.*—Medium.

*Color of juice.*—Clear.

*Flavor.*—Sweet and subacid.

*Quality.*—Very good.

Seeds:

*Generally.*—Present; the seeds of the subject variety separate from the pulp with difficulty.

*Average number.*—Variable, three seeds are generally present; occasionally some berries may be found with only two seeds.

*Size.*—Generally — large; the average seed weight is approximately 49.4 mg.

*Length.*—Average.

*Width.*—Medium.

*Form.*—Generally — pyriform, with a beak; notched.

*Color.*—Light brown.

*Chalaza.*—Medium. Form — circular, distinct, and sunken.

Use: Fresh market.

Although the new variety of grapevine possesses the described characteristics as a result of the growing conditions prevailing in Delano, Calif., in the Southern part of the San Joaquin Valley, it is to be understood that variations in the usual magnitude and characteristics incident to growing conditions, fertilization, pruning and pest control are to be expected.

Having thus described and illustrated my new variety of grapevine, I claim:

1. A new and distinct variety of grapevine to be denominated varietally as "Rouge", substantially as illustrated and described, and which is characterized principally as to novelty by its production of a red berry which is mature for harvesting approximately September 10 to October 15 in Delano, Calif., said grapes maturing in approximately the same season as the fruit produced by the Emperor grapevine (unpatented) which it most closely resembles but from which it is distinguished by producing berries which are mature for commercial harvesting approximately two to three weeks before the Emperor grapevine and which further has leaves having a distinctive U-shaped petiolar sinus and which further has cluster size and color which are distinctively different from the Emperor variety of grapevine.

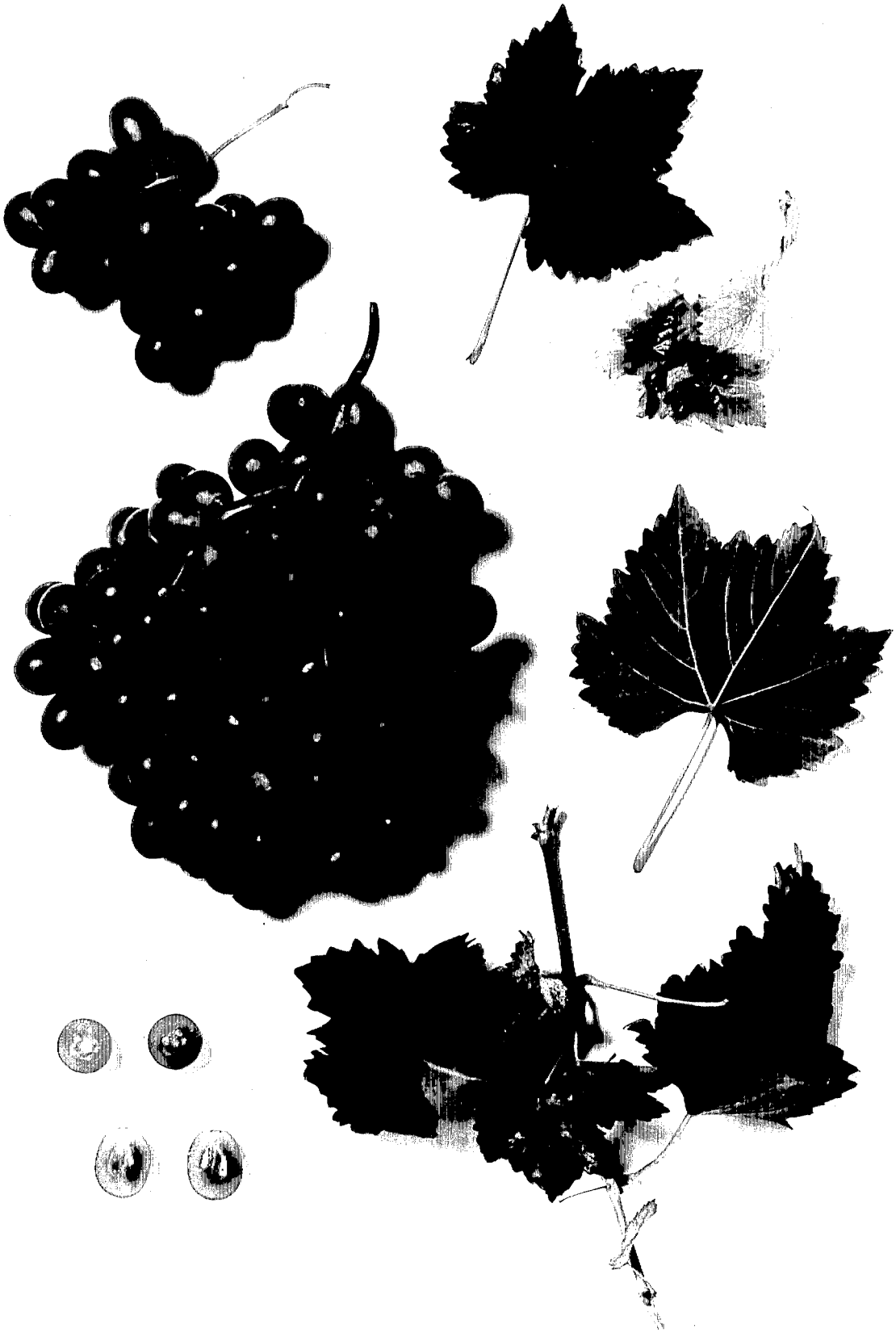

* * * * *